United States Patent [19]

Freedman

[11] 3,950,326
[45] Apr. 13, 1976

[54] CIS OR TRANS-6-SUBSTITUTED-11-AMINOALK-YLIDENEMORPHANTHRIDINES
[75] Inventor: Jules Freedman, Thiensville, Wis.
[73] Assignee: Richardson-Merrell Inc., Wilton, Conn.
[22] Filed: Dec. 6, 1973
[21] Appl. No.: 422,438

[52] U.S. Cl. .......................... 260/239 D; 260/240 R
[51] Int. Cl.² ........................................ C07D 223/24
[58] Field of Search ...................... 260/239 D, 240 R

[56] References Cited
UNITED STATES PATENTS
3,692,906   9/1972   Doge ........................... 260/239 D X
FOREIGN PATENTS OR APPLICATIONS
1,207,116   9/1970   United Kingdom ............. 260/239 D
696,473     9/1953   United Kingdom ............. 260/239 D

*Primary Examiner*—Richard J. Gallagher
*Assistant Examiner*—D. B. Springer
*Attorney, Agent, or Firm*—William J. Stein; Eugene O. Retter; George W. Rauchfuss, Jr.

[57] ABSTRACT

Pure cis or trans-6-substituted-11-aminoalkylidenemorphanthridines are prepared by treating the corresponding cis or trans-5,6-dihydromorphanthridines with oxygen in the presence of a platinum on carbon catalyst. Among the compounds prepared are:
cis-2-Chloro-11-(3-dimethylaminopropylidene)-6-phenylmorphanthridine, and
trans-2-Chloro-11-(3-dimethylaminopropylidene)-6-methylmorphanthridine.

The compounds are useful as antihypertensive and anti-Parkinson agents.

1 Claim, No Drawings

CIS OR TRANS-6-SUBSTITUTED-11-AMINOALK-YLIDENEMORPHANTHRIDINES

BACKGROUND OF THE INVENTION

Methods of preparing 6-substituted-11-aminoalkylidenemorphanthridines are described in Belgian Pat. No. 732,405, British Patent No. 1,207,116, and U.S. Pat. No. 3,692,906. Among the methods described are processes for dehydrogenating the corresponding 5,6-dihydromorphanthridine with oxidizing agents such as chromic acid, peroxide, permanganate or manganese dioxide.

DETAILED DESCRIPTION

The method of the present invention relates to the preparation of compounds of the formula:

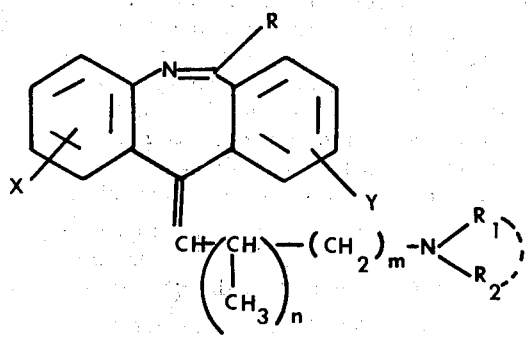

in which $n$ and $m$ are 0 to 3, R is a lower alkyl of 1 to 4 carbon atoms, phenyl or a nuclear substituted phenyl such as p-chlorophenyl and p-methoxyphenyl, $R_1$ and $R_2$ are hydrogen, lower alkyl of 1 to 4 carbon atoms or an aralkyl of 7 to 13 carbon atoms such as benzyl, phenethyl or phenylisopropyl, and X and Y are hydrogen, fluoro, chloro, bromo, trifluoromethyl, hydroxy, lower alkyl of 1 to 4 carbon atoms or a lower alkoxy such as methoxy, ethoxy or propoxy.

In the preferred practice of the invention a pure cis or trans isomer of a corresponding 6-substituted-5,6-dihydromorphanthridine is dissolved in dilute hydrochloric acid, a 5% platinum on carbon catalyst is added and the mixture is heated to reflux and maintained at reflux while oxygen is bubbled through the mixture until the dehydrogenation is essentially complete. Normally the reaction proceeds to completion in about four hours. The desired final product may be isolated from the reaction mixture by crystallization or chromatographic techniques.

The process may be illustrated as follows:

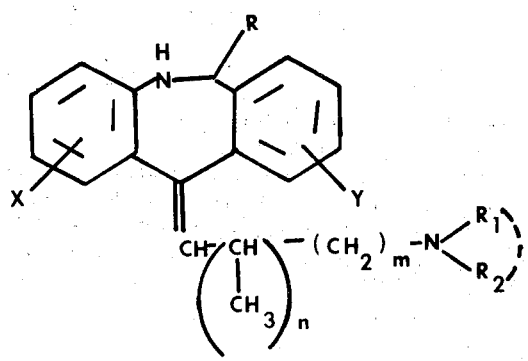

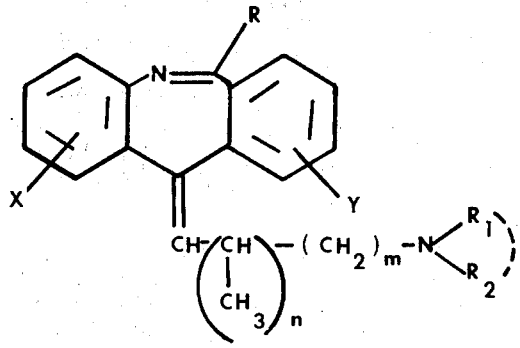

in which all of the symbols are as previously defined.

Representative of the 5,6-dihydromorphanthridines which may be used as starting materials are the following:

cis-2-Chloro-11-(3-dimethylaminopropylidene)-6-methyl-5,6-dihydromorphanthridine,
cis-2-Chloro-11-(3-dimethylaminopropylidene)-6-phenyl-5,6-dihydromorphanthridine,
trans-2-Chloro-11-(3-dimethylaminopropylidene)-6-methyl-5,6-dihydromorphanthridine, and
trans-2-Chloro-11-(3-dimethylaminopropylidene)-6-phenyl-5,6-dihydromorphanthridine.

These 5,6-dihydromorphanthridines may be prepared from the corresponding morphanthridines which are not substituted in the 6-position by reacting such morphanthridines with a Grignard reagent under standard Grignard conditions. The unsubstituted morphanthridines are disclosed in U.S. Pat. No. 3,699,099. The process of preparing the 5,6-dihydromorphanthridines may be diagrammed as follows:

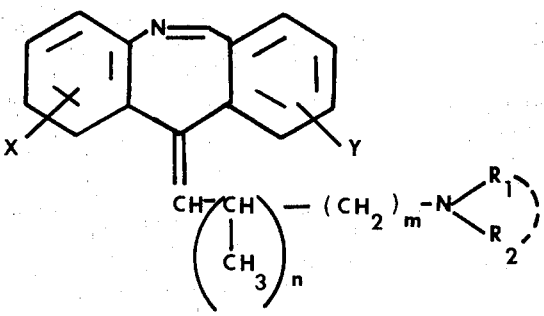

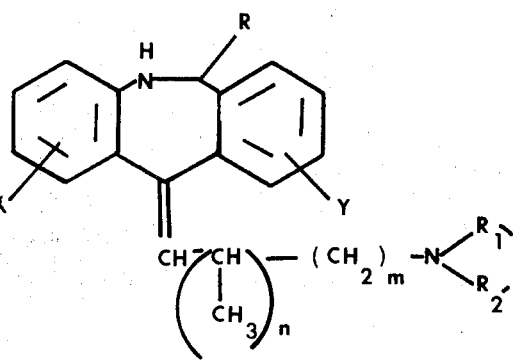

Representative of the final compounds that may be prepared by the method of the present invention are:
cis-2-Chloro-11-(3-dimethylaminopropylidene)-6-methylmorphanthridine,
cis-2-Chloro-11-(3-dimethylaminopropylidene)-6-phenylmorphanthridine,
trans-2-Chloro-11-(3-dimethylaminopropylidene)-6-methylmorphanthridine, and
trans-2-Chloro-11-(3-dimethylaminopropylidene)-6-phenylmorphanthridine.

The methyl substituted compounds are disclosed in U.S. Pat. No. 3,692,906 and are useful as antihypertensive agents and antitremor agents. When employed as pharmaceutical agents, they will, of course, be incorporated in pharmaceutical compositions comprised of diluents and flavoring agents as well as the active ingredients.

When either the cis or the trans form of the compound possesses activity and the corresponding isomer does not, it is extremely important that the active isomer be obtained in as pure a form as possible. The method of the present invention makes it possible to prepare such pure isomers without going through extensive separation procedures.

The practice of the present invention is further illustrated by the following examples:

EXAMPLE 1 cis-2-Chloro-11-(3-dimethylamino-propylidene)-6-methylmorphanthridine

A solution of 16.8 g (0.05 M) of cis-2-chloro-11-(3-dimethylaminopropylidene)-6-methyl-5,6-dihydromorphanthridine in 840 ml. of 0.3 N hydrochloric acid with 1.7 g. of 5% platinum on carbon and 1.7 g. of Darco is brought to reflux and oxygen is bubbled through at 1.7 cu.ft/hour for 4.5 hours. The flask is cooled and toluene followed by 10% sodium hydroxide solution is added with stirring. The mixture is filtered and the toluene layer separated, washed with water and dried over potassium carbonate. The solvent is removed and the residue distilled in a Kugelrohr apparatus at 140°–150°/0.2 mm. to give 15.1 g. of a yellow-brown oil which is shown to be contaminated with some unoxidized material. Reoxidation in 1.5 liters of 0.3 N hydrochloric acid with 1.5 g. of platinum on carbon and 1.5 g. of Darco and oxygen at 1.5 cu.ft/hour for two hours eliminates traces of the starting material. Workup as described above gives 13.1 g. of oil from the toluene. Chromatography on 300 g. of silica and elution with toluene-diethylamine (98:2) gives 6.9 g. of product. Kugelrohr distillation gives 6.3 g. of cis-2-chloro-11-(3-dimethylaminopropylidene)-6-methylmorphanthridine at 125°–133°/2 mm.

Anal. Calcd. for $C_{20}H_{21}ClN_2$: C, 73.94; H, 6.51; Cl, 10.91; N, 8.62. Found: C, 73.89; H, 6.65; Cl 10.81; N, 8.63.

EXAMPLE 2 cis-2Chloro-11-(3-dimethylamino propylidene)-6-phenylmorphanthridine

A mixture of 14.3 g. (0.037 M) of cis-2-chloro-11-(3-dimethylaminopropylidene)-6-phenyl-5,6-dihydromorphanthridine, 1.5 liters of 0.3 N hydrochloric acid, 1.5 g. of platinum on carbon and 1.5 g. of Darco is heated to reflux and oxygen is bubbled through at a rate of 1.5 cu.ft/hour for five hours. After workup as described in Example 1, the toluene residue is crystallized from 50 ml. of hot acetonitrile. The solid, 8.3 g., m.p. 107°–109°, is twice recrystallized from 50 ml. of acetonitrile to give 5.3 g. of cis-2-chloro-11-(3-dimethylaminopropylidene)-6-phenylmorphanthridine, m.p. 111°–114°.

Anal. Calcd. for $C_{25}H_{23}ClN_2$: C, 77.60; H, 5.99; Cl, 9.16; N, 7.24 Found: C, 77.48; H, 6.08; Cl, 9.12; N, 7.27.

EXAMPLE 3 trans-2-Chloro-11-(3-dimethylamino-propylidene)-6-methylmorphanthridine

A mixture of 8.0 g. of 2-chloro-11-(3-dimethylamino-propylidene)-6-methyl-5,6-dihydromorphanthridine, 1.6 g. of 5% platinum on carbon, and 400 ml. of 0.3 N hydrochloric acid is heated to reflux and oxygen bubbled through at a rate of 0.8 cu.ft/hour for four hours. The mixture is cooled and filtered through Celite. After making basic with sodium hydroxide, the oil is extracted into ether and the extracts washed with saturated sodium chloride and dried over potassium carbonate. Removal of the solvent gives 7.3 g. of oil which is purified by chromatography on 400 g. of silica. Elution with toluene-methanol (4:1) and Kugelrohr distillation at 120°–125°/0.2 mm. give 5.2 g. of trans-2-chloro-11-(3-di- methylaminopropylidene)-6-methylmorphanthridine as a yellow oil which is identical to the material prepared by cyclization of N,N-dimethyl-3-(o-acetamidobenzhydrilidene)propylamine.

EXAMPLE 4 trans-2-Chloro-11-(3dimethylamino-propylidene)-6-phenylmorphanthridine

The procedure of Example 3 is followed with 6 g. of trans-2-chloro-11-(3-dimethylaminopropylidene)-6-phenyl- 5,6-dihydromorphanthridine, 1 g. of catalyst, and 600 ml. of 0.3 N hydrochloric acid. The oxygen rate is 0.6 cu.ft/hour for four hours. Workup gives the product as a solid (5.8 g.) on treatment with sodium hydroxide. Chromatography on 350 g. of silica and elution with toluene-methanol (9:1) gives the product as a yellow oil (2.2 g.). Kugelrohr distillation of the product at 145°–150°/0.2 mm. gives 1.7 g. of trans-2-chloro-11-(3-dimethylaminopropylidene)-6-phenylmorphanthridine.

Anal. Calcd. for $C_{25}H_{23}ClN_2$: C, 77.60; H, 5.99; Cl, 9.16; N, 7.24. Found: C, 77.84; H, 6.32; Cl, 8.91; N, 7.00.

I claim:
1. The method of preparing a pure cis or trans isomer of a compound of the formula:

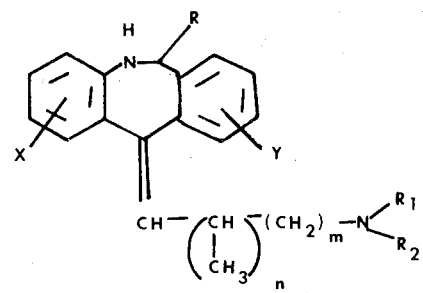

in which $n$ and $m$ are 0 to 3, R is a lower alkyl of 1 to 4 carbon atoms, $R_1$ and $R_2$ are hydrogen, a lower alkyl of 1 to 4 carbon atoms or an hydrocarbon aralkyl of 7 to 13 carbon atoms, X and Y are hydrogen, halo or trifluoromethyl, which comprises the steps of dissolving a pure cis or trans isomer of a compound of the formula:

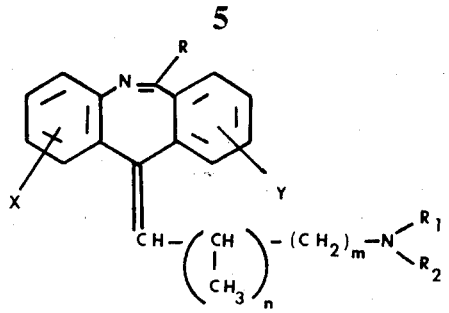
in dilute hydrochloric acid and then passing oxygen through the solution in the presence of a platinum on carbon catalyst under reflux conditions to effect dehydrogenation.
* * * * *

UNITED STATES PATENT AND TRADEMARK OFFICE
CERTIFICATE OF CORRECTION

PATENT NO. : 3,950,326
DATED : April 13, 1976
INVENTOR(S) : Jules Freedman

It is certified that error appears in the above-identified patent and that said Letters Patent are hereby corrected as shown below:

Claim 1, first formula reads:

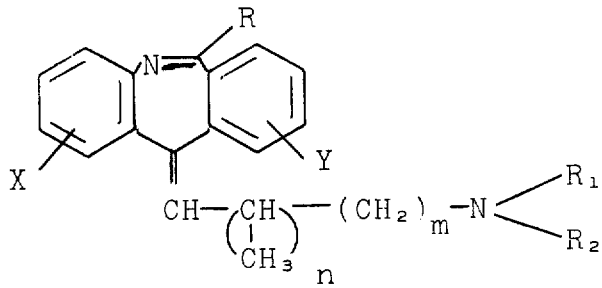

and should read:

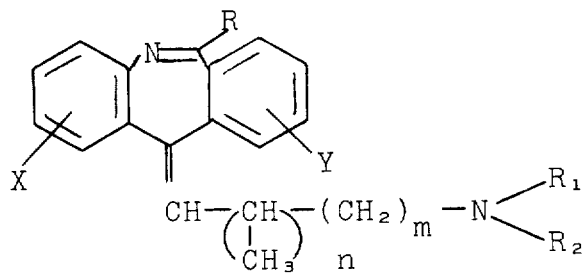

Claim 1, second formula reads:

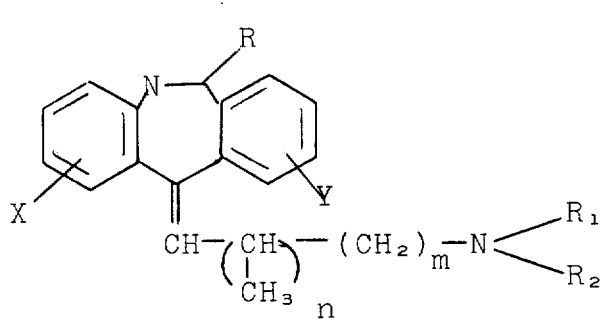

UNITED STATES PATENT AND TRADEMARK OFFICE
CERTIFICATE OF CORRECTION

PATENT NO. : 3,950,326
DATED : April 13, 1976
INVENTOR(S) : Jules Freedman

It is certified that error appears in the above-identified patent and that said Letters Patent are hereby corrected as shown below:

and should read:

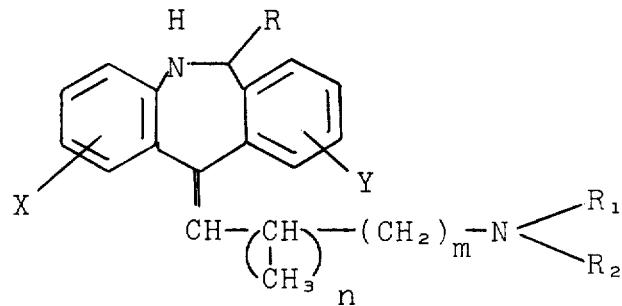

$$\text{Signed and Sealed this}$$

Seventh Day of March 1978

[SEAL]

Attest:

RUTH C. MASON
Attesting Officer

LUTRELLE F. PARKER
Acting Commissioner of Patents and Trademarks